US008822713B2

(12) United States Patent
Longeau et al.

(10) Patent No.: US 8,822,713 B2

(45) Date of Patent: Sep. 2, 2014

(54) POLYMERIZABLE COORDINATION COMPLEXES AND POLYMERIC MATERIALS OBTAINED FROM SAID MONOMERS

(75) Inventors: Alexia Balland Longeau, Tours (FR); Stéphane Cadra, Saint Avertin (FR); Jérôme Thibonnet, Veigne (FR)

(73) Assignee: Comissariat a l'Energie Atomique et aux Energies Alternatives, Paris (FR)

( * ) Notice: Subject to any disclaimer, the term of this patent is extended or adjusted under 35 U.S.C. 154(b) by 207 days.

(21) Appl. No.: 13/509,546

(22) PCT Filed: Nov. 17, 2010

(86) PCT No.: PCT/EP2010/067689

§ 371 (c)(1),
(2), (4) Date: May 16, 2012

(87) PCT Pub. No.: WO2011/061229

PCT Pub. Date: May 26, 2011

(65) Prior Publication Data

US 2012/0217432 A1 Aug. 30, 2012

(30) Foreign Application Priority Data

Nov. 19, 2009 (FR) ..................................... 09 58190

(51) Int. Cl.

| | |
|---|---|
| ***C07F 7/00*** | (2006.01) |
| ***C07F 7/28*** | (2006.01) |
| ***C08F 12/08*** | (2006.01) |
| ***C08F 12/26*** | (2006.01) |

(52) U.S. Cl.

USPC ............... 556/51; 556/54; 526/240; 526/241; 526/311; 526/312; 526/346

(58) Field of Classification Search

USPC ............. 556/51; 524/413, 440, 403; 526/240

See application file for complete search history.

(56) References Cited

U.S. PATENT DOCUMENTS

| | | | | |
|---|---|---|---|---|
| 6,599,414 B1 * | 7/2003 | Virnig et al. | .................. | 205/581 |
| 6,749,811 B2 * | 6/2004 | Murray | ........................... | 422/91 |

FOREIGN PATENT DOCUMENTS

| | | | | |
|---|---|---|---|---|
| CN | 101704910 B * | 8/2011 | ............. | C08F 10/00 |
| EP | 0 584 988 A | 3/1994 | | |

OTHER PUBLICATIONS

Diaz, F.R.; Tagle, L.H.; Alvarez, F.A. Bol. Soc. Chil. Quim. 1991, 36, 253-258.*

Southard et al. Synthesis 2006, 15, 2475-2477.*

Buyuktas et al. Transition Met. Chem. 2006, 31, 56-61.*

Davidson et al. Polyhedron, 2007, 26, 975-980.*

Zhang et al. (CN 101704910 B), abstract and translation in English.*

Southard, et al., "Heck Cross-Coupling for Synthesizing Metal-Complexing Monomers", Synthesis, Georg Thieme Verlag, Stuttgart, No. 15, Aug. 1, 2006, pp. 2475-2477, XP009135738.

Diaz, et al., "Synthesis and characterization of polymers derived from salicylaldoxime and their corresponding chelates with copper (II) or iron (III)", Boletin, De La Sociedad Chilena de Quimica, Sociedad Chilena de Quimica, Concepcion, vol. 36, No. 4, Jan. 1, 1991, pp. 253-258.

Database Beilstein, Beilstein Institute for Organic Chemistry, Frankfurt-Main, DE, Database accession No. BRN 197381 * abrégé & Freund, et al., Chemische Berichte, vol. 36, 1903, p. 1533, XP002590737, Copyright 2007-2010.

International Search Report and Written Opinion issued on Dec. 28, 2010 for International Application No. PCT/EP2010/067689.

Preliminary Report on Patentability issued on Nov. 17, 2010 for International Application No. PCT/EP2010/067689.

* cited by examiner

*Primary Examiner* — Rip A. Lee

(74) *Attorney, Agent, or Firm* — Knobbe, Martens, Olson & Bear, LLP

(57) ABSTRACT

Coordination complexes of at least one metal element with at least one aromatic monomer are provided. The at least one aromatic monomer may comprise at least one aromatic ring, which ring comprising at least one ethylenic group, at least one hydroxide group —OH, at least one oxime group and salts thereof. The metal element may be in the form of a metal alkoxide.

13 Claims, No Drawings

POLYMERIZABLE COORDINATION COMPLEXES AND POLYMERIC MATERIALS OBTAINED FROM SAID MONOMERS

RELATED APPLICATIONS

This application is a U.S. National Phase of International Application No. PCT/EP2010/067689, filed Nov. 17, 2010, designating the U.S., and published in French as WO 2011/061229 on May 26, 2011 which claims the benefit of French Patent Application No. 09 58190 filed Nov. 19, 2009.

TECHNICAL FIELD

The present invention relates to novel polymerizable coordination complexes comprising metal elements, such as titanium, zirconium, hafnium, vanadium, niobium, tantalum, and to polymeric materials resulting from the polymerization of said complexes.

These coordination complexes and the materials obtained by polymerization of the latter find their application in the global field of the applications specific to polymeric materials doped with metal elements, such as supported catalysis, luminescent materials, magnetic materials, ion imprint materials. In particular they find their application in the elaboration of laser targets used during fusion experiments by inertial confinement.

The general field of the invention is thus that of polymeric materials doped with one or several metal elements.

BACKGROUND

Considering the extremely vast field of application of this type of materials, many teams have focused their research on methods for elaborating such materials.

A first strategy consisted of impregnating polymeric materials with metal salt solutions.

Thus, Rinde et al. in U.S. Pat. No. 4,261,937 describe a method for preparing polymeric foams doped with a metal element, consisting of pouring a polymeric gel into an aqueous solution comprising a salt of said metal element. The gel is then put into the presence of a series of solvents with decreasing polarity, in order to remove the introduced water. Each solvent used should be capable of solubilizing the preceding solvent and is saturated by the selected metal salt.

This method however has the major drawback that the distribution of the metal element cannot be perfectly homogeneous at an atomic level, since crystallization phenomena of metal salts occur upon drying which is followed by the formation of nano- or micro-crystals in the material. On the other hand, because impregnation is achieved on a polymeric gel, diffusion of the metal elements does not occur in the totality of the gel.

Other authors have used alternatives of this type of strategy.

Thus, Mishra et al., in *Plasma Phys. Control. Fusion* 43 (2001) 1723-1732, describe the preparation of polystyrene microballoons doped with ultra-fine metal particles comprising the following steps:

- a step for forming an emulsion comprising an aqueous phase and an organic phase comprising polystyrene, in which ultra-fine metal particles are dispersed;
- a step for dispersing the aforementioned emulsion into a second aqueous phase, by means of which a triphasic emulsion is obtained;
- a step for removing the organic phase, letting polystyrene balloons subsist, doped with metal particles, containing water;

- a step for drying said polystyrene balloons.

A second strategy consisted of no longer doping the materials after polymerization of the latter, but of acting upstream from the polymerization step by putting the metal element in contact with the polymerization medium, notably by using monomers bearing the desired dopant metal, depending on whether the metal is an integral part of the monomer molecule (in which case one refers to metal monomers) or is bound to the latter by means of a complexation reaction.

Thus, certain authors have focused their research work on the synthesis of vinyl monomers comprising metal elements or capable of being doped with metal elements, such as titanium.

This is the case of Miele-Pajot et al., in *J. Mater. Chem.,* 1999, 9, 3027-3033, who describe the formation of a titanium complex obtained by reaction of a titanium alkoxide, titanium tetraisopropoxide, with cis-but-2-ene-1,4-diol $HO—CH_2—CH═CH—CH_2—OH$, which complex is then put into contact with a polymerization medium comprising styrene and divinylbenzene, in order to obtain polystyrene foams doped with titanium. However, the embodiment described in this document has the following drawbacks:

- the titanium complex is unstable in an aqueous medium and notably in the polymerization medium, this instability may be expressed by cleavage of the metal-ligand bond;
- the titanium complex thus degrades, during the polymerization of the latter with styrene and divinylbenzene, thereby generating low incorporation of titanium in the final polymeric material, the titanium mass percentage of the polymeric materials not exceeding 1.5%.

Therefore there exists a real need for coordination complexes, which are stable in an aqueous medium, and notably when they are put into the presence of a polymerization medium and consequently with which polymeric materials doped with metal elements may be obtained, the doping level of which is controlled and is, because of the stability of the applied complexes, directly related to their introduction level in the polymerization medium.

DESCRIPTION OF CERTAIN INVENTIVE ASPECTS

Thus, the invention relates, according to a first object, to a coordination complex of at least one metal element with at least one aromatic monomer comprising at least one aromatic ring, said ring comprising at least one ethylenic group, at least one hydroxide group —OH, at least one oxime group and the salts of the latter, said metal element being in the form of a metal alkoxide.

It is specified that by a coordination complex is conventionally meant a polyatomic structure comprising the metal element around which groups (in this case, the —OH and oxime groups) belonging to at least one monomer, are bound through coordination bonds, the coordination bond being created by providing an electron doublet belonging to said groups in an empty orbital of the metal element.

The coordination complexes of the invention have the following advantages:

- they are stable in an aqueous medium, and notably in a complexed form with metal elements, this stability lying in the stability of the metal-ligand bond of the monomers in the complexed form;
- they may be polymerized in order to obtain polymeric materials with a controlled dopant level (this doping level may be very high), because of their stability in the polymerization media;

they are polymerizable, optionally in the presence of other comonomers, both in an organic medium and in an emulsion (for example, a mixture of water and of one or several organic solvents).

Particular monomers entering the constitution of the complexes of the invention fit the following formula (I):

(I)

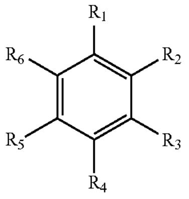

wherein:

$R_1$ is an ethylenic group;

$R_2$, $R_3$, $R_4$, $R_5$ and $R_6$ represent independently of each other, a hydrogen atom, a —OH group, an amine group, a —CHO group, an oxime group, a hydrazone group, a carboxyl group —COOH, a halogen atom, a trialkylsilane group, and the optional salts thereof, provided that at least one of the groups $R_2$ to $R_6$ represents an —OH group and at least one of the groups $R_2$ to $R_6$ represents an oxime group.

Before entering more details on the definition of the monomers of the invention, we specify the following definitions.

By amine group, is conventionally meant a primary amine group —$NH_2$, a secondary amine group (i.e. an amine group for which one of the hydrogen atoms initially borne by the nitrogen atom is substituted with another group, such as an alkyl group) or a tertiary amine group (i.e., an amine group for which the two hydrogen atoms initially borne by the nitrogen atom are substituted with another group, such as an alkyl group).

By an oxime group, is conventionally meant a group comprising the function —C═N—OH, for example a group fitting the formula —CR'═NOH, wherein R' represents a hydrogen atom, an alkyl group, an aryl group, an alkylaryl group, a perfluoroalkyl group, a perfluoroaryl group, a perfluoroalkylaryl group, an acyl group, a carbonyl group, a trialkylsilane group.

By hydrazone group, is conventionally meant a group comprising the function —C═N—N—, for example a group fitting the formula —CR'═N—NR"R'", wherein R', R" and R'" represent independently a hydrogen atom, an alkyl group, an aryl group, an alkylaryl group, a perfluoroalkyl group, a perfluorary group, a perfluoroalkylaryl group, an acyl group, a carbonyl group, a trialkylsilane group.

By halogen atom is meant according to the invention an atom selected from fluorine, chlorine, bromine and iodine.

By alkyl group, is conventionally meant, according to the invention in the foregoing and in the following, a linear or branched alkyl group comprising from 1 to 20 carbon atoms, a cyclic group comprising from 3 to 20 carbon atoms. From these groups, mention may be made of methyl, ethyl, n-propyl, i-propyl, n-butyl, n-dodecanyl, i-butyl, t-butyl, cyclopropyl, cyclohexyl groups. These groups may comprise in their chain one or several atoms selected from O, S, Se and/or N.

By aryl group, is conventionally meant, according to the invention in the foregoing and in the following, a group of 6 to 20 carbon atoms. From these groups, mention may be made of benzyl, naphthyl, tolyl, biphenyl groups.

By alkylaryl groups, is conventionally meant, according to the invention in the foregoing and in the following, an aryl group with the same definition as the one given earlier, said group being substituted with at least one alkyl chain, which may include one or several atoms of O, N, Se and/or S.

By perfluoroalkyl, perfluoroaryl, perfluoroalkylaryl group, are meant groups for which the hydrogen atoms are totally substituted with fluorine atoms (the alkyl, aryl groups meeting the same definition as the one given earlier). For example, mention may be made of trifluoromethyl —$CF_3$, perfluoroethyl, perfluorobutyl, perfluoropropyl, perfluoropentyl, perfluorophenyl $C_6F_5$—, perfluorobiphenyl, perfluorobenzyl.

As mentioned above, the monomers include at least on one aromatic ring, at least one —OH group and at least one oxime group located on said aromatic ring.

Preferably, the —OH group and the oxime group are located in an ortho position relatively to each other on a same aromatic ring, for example a phenyl ring.

Thus, a particular monomer fits the following formula (II):

(II)

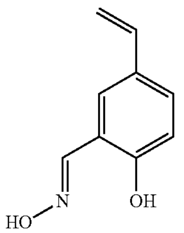

The monomers according to the invention may be simply elaborated from inexpensive starting compounds, notably natural compounds such as salicylaldehyde.

Thus, starting with salicylaldehyde, it is possible to make the particular monomer mentioned above by the following simple steps:

- a halogenation step by electrophilic substitution of a hydrogen atom borne by the phenyl group of salicylaldehyde, this step may consist in an iodination step by action on the salicylaldehyde of an iodine salt (such as chlorine iodide) in an acetic medium, by means of which 5-iodosalicylaldehyde is obtained;
- a step for forming the oxime function by reaction of hydroxylamine on the 5-iodosalicylaldehyde, by means of which 5-iodosalicylaldoxime is obtained;
- a step for introducing the ethylenic group by reaction of 5-iodosalicylaldoxime with a vinyltin compound in the presence of a catalyst based on platinum (such as $Pd(PPh_3)_4$ with Ph indicating a phenyl group).

Such a method may be summarized by the following reaction scheme:

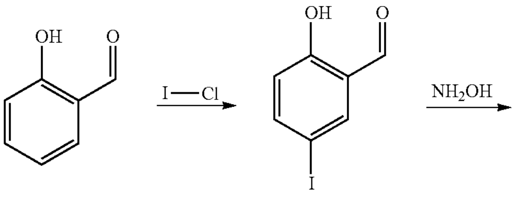

-continued

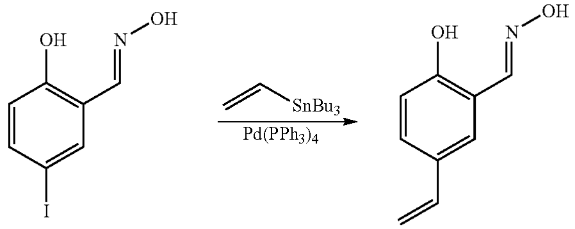

(IV)

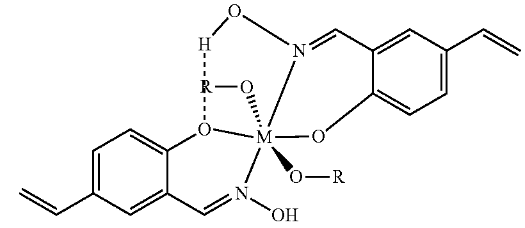

Generally, starting with a compound comprising an aromatic ring (for example styrenic derivatives, salicylaldehyde, salicylaldoxime, phenol), introduction of the primordial groups of the monomers of the invention, i.e. if these groups are not already present in the starting compounds, the ethylenic, hydroxyl and/or oxime groups, is quite within the reach of one skilled in the art, by simple synthesis techniques.

The monomers may be made, under mild conditions, notably when the matter is of introducing an ethylenic group onto a halogenated phenyl group, this introduction may be carried out at an atmospheric pressure with light heating (for example, at most 50° C.).

The aforementioned metal element may be an alkaline metal, an earth alkaline metal, a transition metal, such as Ti, Zr, Hf, V, Nb, Ta, a lanthanide, an actinide as well as the elements Al, Ga, Ge, In, Sn, Sb, Tl, Pb, Bi or Po; this metal element may appear as a metal alkoxide.

As an example, mention may be made of titanium alkoxides, such as titanium isopropoxide, titanium ethoxide, zirconium alkoxides, such as zirconium n-butoxide, niobium alkoxides, such as niobium ethoxide.

The aforementioned coordination complexes may be obtained by putting monomers as defined above, optionally in the form of salts, into contact with a metal alkoxide.

The reaction for forming the complexes may be carried out in a hydrated or anhydrous organic medium, in the presence of an ambient atmosphere saturated with nitrogen or argon.

Specific coordination complexes according to the invention may appear as clusters comprising one or several monomer molecules surrounding one or several metal elements in the form of metal alkoxides.

As examples, mention may be made of the clusters fitting the following formulae (III) and (IV):

(III)

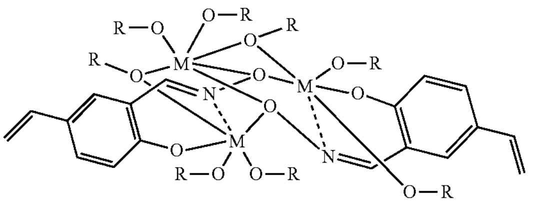

with M representing a metal element, such as Ti, and R representing an alkyl group, such as an isopropyl group, an ethyl group;

with M representing a metal element, such as Zr, Nb, and R representing an alkyl group, such as an n-butyl group, an ethyl group.

The complexes of the invention are intended to be used for making polymeric materials doped with at least one metal element.

Thus, the invention according to a third object relates to a method for preparing a polymeric material doped with at least one metal element comprising a step for polymerizing at least one coordination complex as defined above.

The method of the invention thus has the following advantages:

- it allows incorporation into polymeric materials of a wide diversity of metal elements, because the bond between the metal elements and the monomer(s) is effected by a coordination bond;
- it allows distribution of the metal element at an atomic scale;
- it allows incorporation of high levels of metal element, said level depending on the amount of coordination complex set into play during the polymerization step.

Conventionally, the polymerization step of the method of the invention takes place, in addition to the presence of the coordination complex, in the presence optionally of a polymerization initiator and optionally of a porogenic solvent and of one or several comonomers.

The polymerization mode may be of any type, such as thermal polymerization (for example, by heating from 50 to 150° C.), such as photochemical polymerization in the presence of ultra-violet radiation.

The polymerization initiator may be a radical initiator conventionally selected from peroxides, azonitriles (such as 2,2-azobisisobutyro-nitrile), azoesters, azoamides.

The initiator may be introduced, into the polymerization medium, according to variable amounts, for example according to amounts which may range from 0 to 50% by mass, based on the total mass of monomers set into play.

The porogenic solvent may be a polar, an apolar organic solvent and may be selected from ether solvents (such as tetrahydrofurane), dimethylsulfoxide, phthalate solvents, (such as dimethylphthalate, dibutylphthalate), alcoholic solvents (such as methanol, ethanol), aromatic solvents (such as toluene, fluorobenzene), ketone solvents.

The polymerization step may be carried out in the presence of one or several comonomers, said comonomers being generally different from the monomers entering the constitution of the coordination complexes.

These comonomers may be selected from styrenic monomers or acrylate monomers.

Advantageously, the comonomers comprise at least two ethylenic groups thereby providing a cross-linker role. The thereby obtained materials have good mechanical toughness.

Comonomers which may be used, may be styrenic monomers of the following formula (V):

(V)

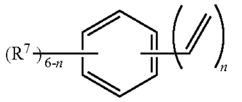

wherein the (6−n) $R^7$ groups, either identical or different, represent a hydrogen atom, an alkyl group, an aryl group, an —O-aryl group, an —O-alkyl group, an acyl group, an alkylaryl group, a halogen atom, said alkyl, aryl, alkylaryl, —O-aryl, —O-alkyl groups being optionally perfluorinated and n is an integer ranging from 1 to 3, n being preferably equal to 2.

In particular, a suitable comonomer may be divinylbenzene, in particular 1,4-divinylbenzene.

Comonomers which may be used may also be acrylate compounds of the following formula (VI):

(VI)

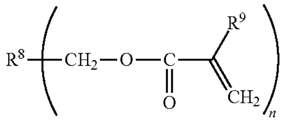

wherein $R^8$ represents an alkyl group, $R^9$ represents H or an alkyl group and n being an integer ranging from 1 to 3.

In particular, a suitable comonomer of this type may be trimethylolpropane triacrylate (known under the acronym TMPTA) of the following formula:

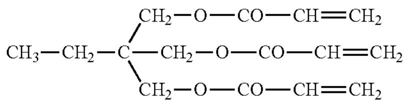

Conventionally, the polymerization step is carried out at a temperature ranging from 40 to 100° C.

According to a particular embodiment of the invention, the polymerization step consists in the copolymerization of a coordination complex of the following formula:

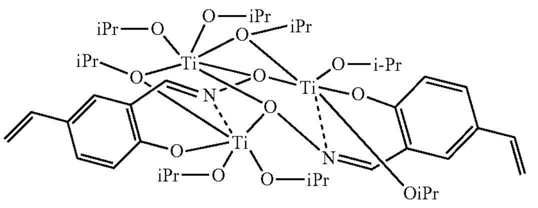

with divinylbenzene, iPr meaning isopropyl or further with trimethylolpropane triacrylate (known under the acronym of TMPTA).

After the polymerization step, a gel is obtained, corresponding to a three-dimensional network, the structure of which is impregnated with the solvent. The gel once it is synthesized, has to be dried, in order to obtain the dry doped polymeric material.

Thus, the method advantageously comprises a step for drying the obtained gel, this step being advantageously a step for supercritical drying with $CO_2$. To do this, this supercritical drying step with $CO_2$ may be preceded with a solvent exchange step consisting of replacing the solvent present in the pores of the gel with a solvent miscible with $CO_2$. With this supercritical drying step with $CO_2$, it is notably possible to preserve the physical integrity of the foam.

By means of the method of the invention, polymeric materials doped with a metal element are obtained, having a high percentage of metal element (which may be greater than 20% by mass) and with a distribution at a molecular scale of the metal element within the material.

Thus, the invention relates to polymeric materials doped with at least one metal element which may be obtained by a method as defined above, the materials conventionally appearing as foams.

These materials may be characterized by a specific gravity ranging from 3 to $250.10^{-3}$ $g \cdot cm^{-3}$ and a specific surface area which may range up to 880 $m^2/g$.

These materials may be used in many fields requiring application of materials doped with metal elements and notably in the elaboration of elements of laser targets used in fusion experiments by inertial confinement in particular.

They may also be used as a catalyst, as luminescent materials or as magnetic materials.

In particular, they may be used as a laser target element.

Finally, they may be used as materials with ionic imprint. To do this, the doped materials obtained with the method of the invention may be subject to an acid treatment, intended to remove part of the complexed metal elements in said material. The vacant sites thus form specific imprints of the specific element of the metal introduced initially. From this treatment, a material results said to be « with an ionic imprint », capable of selectively trapping the « printed » metal element when put into contact with a fluid comprising said metal element. This type of materials may thus be used for selective extraction of metals, notably during reprocessing of nuclear fuel effluents, such as separation of lanthanides, or further decontamination of biological fluids.

The invention will now be described with reference to the following examples given as an illustration and not as a limitation.

DETAILED DISCUSSION OF PARTICULAR EMBODIMENTS

Example 1

The present example illustrates the preparation of a monomer of the following formula (II):

(II)

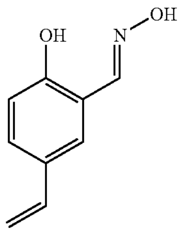

This monomer is produced according to the following synthesis scheme:

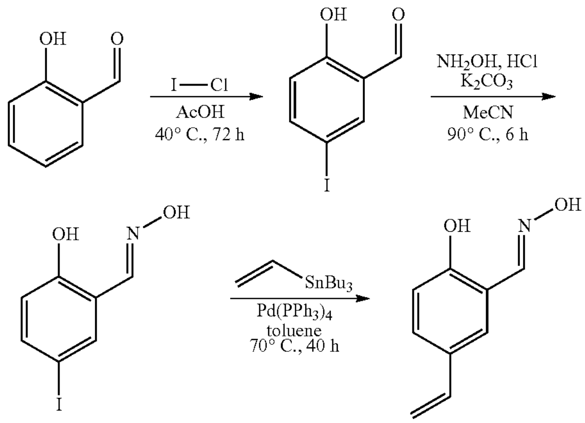

AcOH meaning acetic acid, MeCN meaning acetonitrile, Ph meaning phenyl, and Bu meaning n-butyl.

Thus, the first step consists of producing 5-iodosalicylaldehyde from salicylaldehyde.

In a 500 mL two-neck flask provided with a condenser, are placed with stirring, 160 mL of glacial acetic acid and 10.4 mL (100 mmol) of salicylaldehyde. A solution of 10 g (1.1 equiv., 110 mmol) of iodine monochloride dissolved in a minimum of acetic acid is then added to the mixture. The reaction is maintained with stirring at T=40° C. for 72 hours. The solvent is then evaporated. The residue is taken up in 100 mL of dichloromethane, washed with 100 mL of an aqueous solution saturated with sodium thiosulfate, 100 mL of a solution saturated with sodium chloride NaCl and 150 mL of distilled water. The organic phase is dried on $MgSO_4$, evaporated and the residue is recrystallized for 24 hours from a minimum of dichloromethane.

The characteristics of the obtained product are the following:

Aspect: yellow powder

Yield: 50%

Melting point: 104° C.

NMR $^1H$ (solvent: $CDCl_3$) δ: 6.80 (1H, d, j=10 Hz); 7.72 (1H, dd, j=2.5 Hz/10 Hz); 7.84 (1H, d, j=2.5 Hz); 9.82 (1H, s); 10.70 (1H, s)

$^{13}C$ NMR (solvent: $CDCl_3$) δ: 80.81; 120.60; 122.96; 142.26; 145.69; 161.60; 195.82.

The second step consists of producing 5-iodosalicylaldoxime from 5-iodosalicyl-aldehyde prepared beforehand.

To do this, 35 mmol (3.5 equiv., 2.40 g) of hydroxylamine hydrochloride are added to a solution of 4 g of $K_2CO_3$ (35 mmol, 3.5 equiv.) and of 5-iodosalicylaldehyde (10 mmol, 2.50 g) in 50 mL of acetonitrile. The mixture is heated to 70° C. with stirring overnight.

At the end of the reaction, the excess $K_2CO_3$ is removed by filtration, the filtrate is evaporated, the residue is taken up in 250 mL of water, and then hydrochloric acid is delicately introduced until a pH of 4 is attained. The solution is then extracted with dichloromethane. The organic phase is dried on $MgSO_4$, filtered and the solvent is then evaporated. The solid is then purified by filtration on silica (eluent:heptane/$Et_2O$ 75/25) and the filtrate is then evaporated.

The characteristics of the obtained product are the following:

Aspect: white powder

Yield: 95%

Melting point: 134° C.

$^1H$ NMR (solvent: $CDCl_3$) δ: 6.80 (1H, d, j=8 Hz); 7.48 (1H, d, j=2 Hz); 7.55 (1H, dd, j=2 Hz/8 Hz); 7.60 (H, s); 8.16 (1H, s); 9.85 (1H, s).

$^{13}C$ NMR (solvent: $CDCl_3$) δ: 80.1; 117.8; 118.2; 138.2; 139.1; 151.2; 156.2.

The third step finally consists of producing 5-vinylsalicylaldoxime from 5-iodo-salicylaldoxime prepared beforehand.

To do this, 3.94 g (15 mmol) of 5-iodo-salicylaldoxime, 30 mL of anhydrous toluene, 879 mg (5 mol %) of $Pd(PPh_3)_4$ and 6,60 mL of vinyltin $CH_2$=CH—$SnBu_3$ (Bu meaning n-butyl) are successively introduced with stirring and in this order into a 100 mL flask dried under Grignard conditions and purged with argon. The mixture is degassed, purged with argon and heated to 70° C. with strong stirring for 72 hours.

At the end of the reaction, the solution is filtered on celite (with the solvent $Et_2O$), the precipitate which forms, is removed by filtration, the solvents are evaporated and the residue is purified through a flash column (eluents: 400 mL of heptane, 500 mL of a heptane/$Et_2O$ mixture 95:5 and heptane/$Et_2O$ mixture 90:10).

The characteristics of the obtained product are the following:

Aspect: white crystals

Yield: 51%

Melting point: 107° C.

$^1H$ NMR (solvent: $CDCl_3$) δ: 5.16 (1H, d, j=14 Hz); 5.60 (1H, d, j=22.5 Hz); 6.64 (1H, dd, j=13 Hz/22.5 Hz); 6.96 (1H, d, j=8 Hz); 7.21 (1H, d, j=2 Hz); 7.39 (1H, dd, j=8 Hz/2 Hz); 7.59 (1H, s); 8.24 (1H, s); 9.95 (1H, s)

$^{13}C$ NMR (solvent: $CDCl_3$) δ: 111.78; 115.77; 116.51; 128.29; 128.55; 129.30; 135.04; 152.53; 156.42.

Example 2

This example relates to the preparation of a complex formed by two molecules of the monomer prepared according to Example 1 with titanium in the form of an alkoxide (titanium isopropoxide): 5-vinylsalicyl-aldoximatotitanium isopropoxide of the following formula:

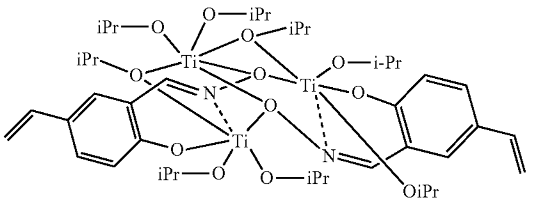

iPr meaning isopropyl.

1.25 g (7.5 mmol) of 5-vinyl-salicyl-aldoxime, 8 mL of anhydrous toluene and 3.25 g (1.5 equiv.; 11.25 mmol) of titanium isopropoxide are introduced into a 15 mL 1-neck flask. The mixture is purged with argon and heated to 50° C. with strong stirring for 3 hours. At the end of the reaction, the solvent is evaporated. In order to remove any trace amount of residual toluene, the red residue is diluted in 5 mL of diethyl ether and is again evaporated.

The characteristics of the obtained product are the following:

Aspect: orangey solid

Yield: 93%

Melting point: 128.8° C.

$^1H$ NMR (solvent: toluene D8): δ 0.99 (12H, m); 1.52 (36H, m); 4.60 (2H, sept); 4.95 (2H, sept.); 5.04 (2H, sept.);

5.18 (2H, sept.); 5.40 (2H, d, j=22 Hz); 6.50 (2H, dd, j=12.5 Hz/22 Hz); 6.80 (2H, d, j=12.5 Hz); 6.98 (2H, d, j=8 Hz) ; 7.01 (2H, d, j=2 Hz) ; 7.20 (2H, dd, j=8 Hz/2 Hz); 8.15 (20H, s)

$^{13}C$ NMR (solvent: toluene D8): δ 24.60; 78.15; 109.98; 117.86; 119.86; 127.93; 129.34; 135.62; 136.64; 152.93; 170.12

Elementary analysis: % by mass Ti: 15.8 ±0.7% (15.3% (theory))

High Resolution Mass Spectrometry (HRMS): 939.3462 (939.3456 (theory)); error +0.6 ppm

Example 3

This example relates to the preparation of a complex formed by two molecules of the monomer prepared according to Example 1 with titanium in the form of an alkoxide (titanium ethoxide): 5-vinylsalicyl-aldoximatotitanium ethoxide of the following formula:

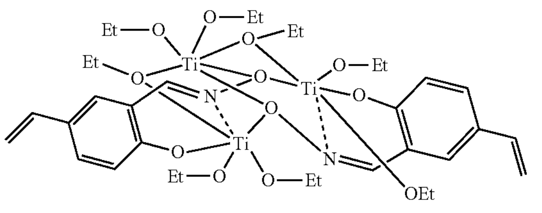

328 mg (2 mmol) of 5-vinylsalicylaldoxime, 2 mL of anhydrous toluene and 0.629 mL (1.5 equiv.; 3 mmol) of titanium ethoxide are introduced into a 5 mL 1-neck flask. The mixture is purged with argon and stirred for 3 hours at room temperature. At the end of the reaction, the solvent is evaporated. In order to remove any trace amount of residual toluene, the red residue is diluted in 5 mL of diethyl ether and is again evaporated.

The characteristics of the obtained product are the following:

Aspect: orangey solid

Yield: 75%

$^{1}H$ NMR (solvent: toluene D8): δ 0.84 (6H, m); 1.26 (6H, m) ; 1.57 (12H, m) ; 4.15 (4H, quad.); 4.55 (8H, m) ; 4.85 (4H, quad.); 4.95 (4H, d); 5.40 (2H, d, j=22 Hz); 6.50 (2H, dd, j=12.5 Hz/22 Hz); 6.80 (2H, d, j=12.5 Hz); 6.98 (2H, d, j=8 Hz) ; 7.01 (2H, d, j=2 Hz) ; 7.20 (2H, dd, j=8 Hz/2 Hz); 8.15 (20H, s)

$^{13}C$ NMR (solvent: toluene D8): δ 18.45; 71.56; 104.91; 115.80; 119.71; 126.39; 128.03; 135.48; 136.64; 157.57; 162.06

Example 4

This example relates to the preparation of a complex formed with two molecules of the monomer prepared according to Example 1 with zirconium in the form of an alkoxide (zirconium n-butoxide): 5-vinylsalicylaldoximatozirconium n-butoxide of the following formula:

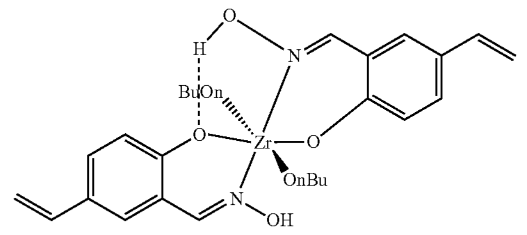

nBu meaning n-butyl.

164 mg (1 mmol) of 5-vinylsalicylaldoxime solubilized in 2 mL of anhydrous n-butanol and 0.5 mL of a solution of zirconium n-butoxide at 80% by mass in n-butanol are introduced into a 5 mL 1-neck flask purged with argon. The mixture is purged with argon and is thoroughly stirred for 2 hours at room temperature.

At the end of the reaction, the obtained yellow precipitate is isolated by filtration and rinsed with 2*10 mL of n-butanol.

The characteristics of the obtained product are the following:

Aspect: yellow solid

Yield: 41%

$^{1}H$ NMR (solvent: DMSO D6): δ 0.86 (12H, t); 1.35 (16H, m) ; 3.37 (4H, t) ; 5.11 (2H, d) ; 5.62 (2H, d) ; 6.63 (2H, dd); 6.85 (2H, d); 7.34 (2H, dd); 7.58 (2H, d); 8.32 (2H, s); 10.22 (1H, s); 11.38 (1H, s)

$^{13}C$ NMR (solvent DMSO D6): δ 19.47; 24.26; 40.30; 66.00; 117.42; 121.89; 123.90; 131.29; 133.77; 134.33; 141.54; 152.87; 161.47

Example 5

This example relates to the preparation of a complex formed with two molecules of the monomer according to Example 1 with niobium in the form of an alkoxide (niobium ethoxide): 5-vinylsalicyl-aldoximatoniobium(V) ethoxide of the following formula:

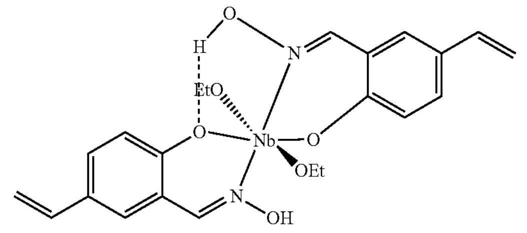

Et meaning ethyl.

164 mg (1 mmol) of 5-vinylsalicyl-aldoxime solubilized in 1.5 mL of absolute ethanol, are introduced into a 5 mL 1-neck flask purged with argon.

The mixture is degassed, and then 160 mg of $Nb(OEt)_5$ are introduced. The mixture is purged with argon and is thoroughly stirred overnight at room temperature.

At the end of the reaction, the solvent is evaporated. The residual red solid is then kept under an inert atmosphere ($N_2$).

Aspect: red solid

Yield: 43%

$^{1}H$ NMR (solvent: DMSO D6): δ 1.05 (6H, t); 3.43 (4H, m); 5.09 (2H, d); 5.64 (2H, d); 6.65 (2H, dd); 6.86 (2H, d); 7.37 (2H, dd); 7.57 (2H, d); 8.31 (2H, s); 10.20 (1H, s); 11.35 (1H, s)

$^{13}C$ NMR (solvent: DMSO D6): δ 19.16; 56.74; 112.37; 117.02; 119.07; 126.32; 128.74; 129.60; 136.55; 147.72; 156.27

Example 6

This example illustrates the preparation of a polymeric material obtained by copolymerization of a complex prepared according to Example 1 with divinylbenzene in the presence of a porogenic solvent: dibutyl phthalate (DBP).

The mixture of monomers is prepared according to the two following methods:

Method A

In a pill-box of 25 mL provided with a stirrer and purged with argon is introduced 1 g of a mixture comprising the complex prepared according to Example 2 and divinylbenzene, 10 mL of dibutyl phthalate, 100 mg of azoisobutyronitrile and 100 mg of a surfactant SPAN 80. The mixture is placed under stirring and is subject to degassing with argon for 10 minutes.

Method B

Two parent stock solutions are prepared in two 25 mL pill-boxes:

- the first consists of 1 g of divinylbenzene, 10 mL of dibutyl phthalate, 100 mg of azoisobutyronitrile and 100 mg of a surfactant SPAN 80;
- the second consists of 1 g of the complex prepared according to Example 2, 10 mL of dibutyl phthalate, 100 mg of azoisobutyronitrile and 100 mg of a surfactant SPAN 80.

The samples taken from both solutions are combined in a 4 mL pill box provided with a stirrer according to the desired doped monomer concentration. The thereby obtained diluted offspring solution is homogenized and is subject to degassing with argon for 3-5 minutes.

The solution of monomers prepared according to Method B is introduced into a series of polypropylene (or silicone) molds purged beforehand with argon. The whole is placed overnight in an oven at 80° C. The thereby obtained polymer gels are then removed from the molds and placed in 25 mL pill boxes containing 15 mL of ethanol. The ethanol of the pill boxes is renewed every 48 hours for one week. This method is called hereafter « a bulk polymerization method » .

The solution of monomers prepared beforehand according to Method A is introduced dropwise via a syringe into a 1 L container containing 300 mL of a 88% polyvinyl alcohol solution at 50 g/L and preheated to 45° C., so as to form a multitude of organic phase beads inside the aqueous phase. The container is then placed horizontally, slightly rotating in a water bath (with a rotary evaporator) at 85° C. for three hours. The thereby obtained polymer beads are recovered, placed in a 25 mL pill box containing 15 mL of distilled water, and then rinsed with 2*15 mL of distilled water and 1*15 mL of ethanol. The beads are kept in ethanol, the solvent being renewed every 48 hours for one week. This method is designated hereafter as « emulsion polymer method» .

The gels thereby obtained by these two polymerization methods are then dried with supercritical carbon dioxide so as to obtain copolymer foams.

Different tests were conducted with different ratios (complex of Example 2/DVB), i.e. complex mass ratios of 50%, 66%, 75% and 100%, by means of which the following mass percentages of titanium element are obtained: 7.65%, 10.1%, 11.47% and 15.3%, the preceding percentages corresponding to the titanium mass percentages based on the total mass of monomers of the solution prepared beforehand (called subsequently the initial titanium mass %).

The obtained foams, for the different aforementioned ratios, were subject to the following measurements:

- measurement of the titanium mass percentage in the foams (this measurement being carried out by microanalysis);
- measurement of the specific surface area by the BET method for foams obtained by the bulk polymerization method.

The results are grouped in the table below.

| Initial Ti mass % | 7.65 | 10.1 | 11.47 | 15.3 |
|---|---|---|---|---|
| Ti mass % in the foam (bulk polymerization method) | 7.9 ± 0.3 | 10.4 ± 0.4 | 12.5 ± 0.5 | 17.5 ± 0.7 |
| Ti mass % in the foam (emulsion polymerization method) | 11.3 ± 0.5 | 17.2 ± 0.7 | 19.3 ± 0.8 | — |
| Specific surface area (in $m^2/g$) of the foams obtained by the bulk polymerization method | 680 ± 60 | 500 ± 50 | — | 345 ± 30 |

A highly significant titanium content in the obtained foams as well as very large specific surface area values emerge from this table.

Example 7

This example illustrates the preparation of a polymeric material obtained by copolymerization of a complex prepared according to Example 2 with trimethylolpropane triacrylate in the presence of a porogenic solvent: dibutyl phthalate (DBP).

The mixture of monomers is prepared according to the following method.

In a 25 mL pill box provided with a stirrer and purged with argon, are introduced 1 g of a mixture comprising the complex according to Example 2 and trimethylolpropane triacrylate, 10 mL of DBP, 100 mg (10% by mass) of surfactant (SPAN 80) and 100 mg (10% by mass) of AIBN. The mixture is placed with stirring and is subject to degassing with argon for 10 minutes.

The mixture of monomers prepared above is polymerized according to a suspension polymerization method in an aqueous continuous phase as explained below.

Preparation of the continuous phase: In a 5 L glass bottle provided with a magnetic stirrer, are introduced 2 L of distilled water. 105 g of polyvinyl alcohol (85% hydrolyzed) are then added with thorough stirring. The mixture is heated to 60° C. with stirring until the solution is perfectly limpid.

Polymerization: 400 mL of continuous phase are sampled and introduced into a 2 L cylindrical glass container (bottle) provided with a ground joint. The solution is preheated to 45° C. 1 mL of polymerization mixture (prepared according to method A) is then introduced into a syringe provided with a needle of dimensions 0.6×25 cm. The phase of monomers is introduced dropwise, the needle immersed inside the continuous phase, so as to form beads of organic phase dispersed in the aqueous phase. The container is then fixed horizontally on a motor-driven axis (for example a cannula of a rotary evaporator). The latter is placed slowly rotating in a water bath at 85° C. for 3 hours. At the end of the polymerization, the water bath is removed and rotation is maintained until the medium cools down to a temperature of ~45° C. The beads of gel are sampled and washed 3 times with 20 mL of distilled water. They are then kept for one week in 25 mL pill-boxes containing 20 mL of absolute ethanol, this ethanol solution being renewed 3 times during this period. The gels are then recovered and dried with supercritical $CO_2$ in order to obtain beads of organic aerogels.

Different tests were conducted with different ratios (complex of Example 2/TMPTA), i.e. complex mass ratios of 25%, 75%, by means of which the following respective titanium element mass percentages are obtained: 6.5% and 19.5% (i.e. respectively in atom %, 1.1 and 3.8 atom %).

What is claimed is:

1. A coordination complex of at least one metal element with at least one aromatic monomer comprising at least one aromatic ring, which ring comprising at least one ethylenic group, at least one hydroxide group —OH, at least one oxime group and salts thereof, said metal element being in the form of a metal alkoxide, wherein the complex comprises one of the following formulas (III) and (IV):

(III)

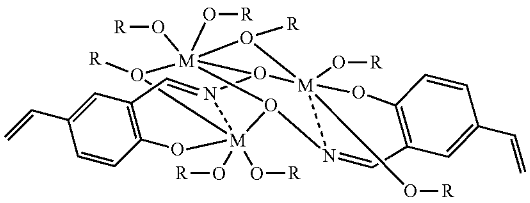

with M representing a metal element and R representing an alkyl group;

(IV)

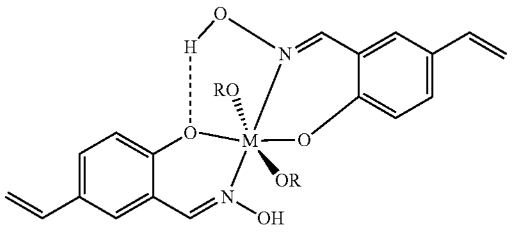

with M representing a metal element and R representing an alkyl group.

2. The complex according to claim 1, wherein the metal element is selected from the group consisting of alkaline metals, earth alkaline metals, transition metals, lanthanide metals, actinide metals, elements Al, Ga, Ge, In, Sn, Sb, Tl, Pb, Bi and Po.

3. The complex according to claim 1, wherein the metal element is titanium.

4. A method for preparing a polymeric material doped with at least one metal element comprising a step of polymerizing at least one coordination complex as defined according to claim 1.

5. The method according to claim 4, wherein the polymerization step is carried out in the presence of one or several comonomers.

6. The method according to claim 5, wherein the comonomer(s) is(are) selected from styrenic monomers and acrylate monomers.

7. The method according to claim 5, wherein the comonomer(s) comprise(s) at least two ethylenic groups.

8. The method according to claim 6, wherein the comonomer(s) fit(s) one of the following formulae (V) or (VI):

(V)

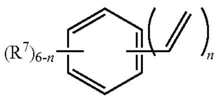

(VI)

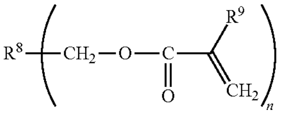

wherein the (6−n) $R^7$ groups, either identical or different, represent a hydrogen atom, an alkyl group, an aryl group, an —O-aryl group, an —O-alkyl group, an acyl group, an alkylaryl group, a halogen atom, said alkyl, aryl, alkylaryl, —O-aryl, —O-alkyl groups being optionally perfluorinated, $R^8$ represents an alkyl group, $R^9$ represents H or an alkyl group and n is an integer ranging from 1 to 3.

9. The method according to claim 8, wherein the comonomer is divinylbenzene.

10. The method according to claim 8, wherein the comonomer is trimethylolpropane triacrylate.

11. The method according to claim 4, comprising, after the polymerization step, a step of supercritical drying a material obtained from the polymerization step with $CO_2$.

12. The method according to claim 4, wherein the polymerization step consists of the copolymerization of a coordination complex of the following formula:

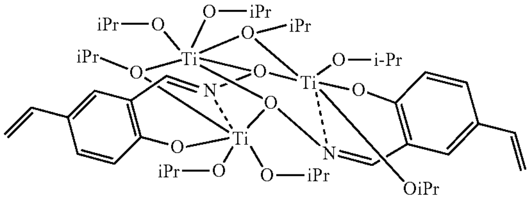

with divinylbenzene or trimethylolpropane triacrylate.

13. A method of separating a metal from a sample containing said metal, comprising:

preparing a polymeric material doped with at least one metal element according to the method of claim 4;

subjecting said material to acid treatment so as to remove part of the metal element from said material, thereby creating vacant sites with specific imprints of the metal element from said material; and exposing said sample to said vacant sites so as to selectively extract said metal from said sample into said vacant sites.

* * * * *